United States Patent [19]
Lemchen et al.

[11] Patent Number: 5,278,756
[45] Date of Patent: Jan. 11, 1994

[54] METHOD AND APPARATUS FOR GENERATING CEPHALOMETRIC IMAGES

[75] Inventors: Marc S. Lemchen, New York, N.Y.; Gary A. Engel, Sherman Oaks, Calif.

[73] Assignee: Dolphin Imaging Systems, Valencia, Calif.

[21] Appl. No.: 578,944

[22] Filed: Sep. 7, 1990

Related U.S. Application Data

[63] Continuation-in-part of Ser. No. 301,499, Jan. 24, 1989, abandoned.

[51] Int. Cl.⁵ ............................................. G06F 15/00
[52] U.S. Cl. .................................. 364/413.28; 433/68
[58] Field of Search ..................... 364/413.28; 433/68, 433/72, 73

[56] References Cited
U.S. PATENT DOCUMENTS 4,197,855 4/1980 Lewin ................................. 128/653
4,528,627 7/1985 Coben ............................ 364/413.28
4,836,778 6/1989 Baumrind ............................. 433/69

Primary Examiner—Roy N. Envall, Jr.
Assistant Examiner—Khai Tran
Attorney, Agent, or Firm—Daniel L. Dawes

[57] ABSTRACT

A method and apparatus for generating a cephalometric tracing directly from a patient by directly generating digitized two- or three-dimensional data from the patient's head to define locations of preselected landmarks thereon from which diagnostic data points required for the cephalometric tracing are computer generated and connected so as to produce a cephalometric tracing. A video recording of the patient's head corresponding to the spatial orientation of the cephalometric tracing at the time of the generation of the data is made, reproduced in visible form to the same scale as the cephalometric tracing and superimposed on the tracing on a video monitor.

23 Claims, 12 Drawing Sheets

METHOD AND APPARATUS FOR GENERATING CEPHALOMETRIC IMAGES

CROSS-REFERENCE TO RELATED APPLICATION

The present application is a continuation-in-part of our co-pending application Ser. No. 07/301,499, filed Jan. 24, 1989, entitled Method For Generating Cephalometric Tracings, now abandoned.

FIELD OF THE INVENTION

This invention relates to the field of orthodontics and, more particularly, to improvements in locating anatomical landmarks for use in the generation of cephalometric tracings used in orthodontic analysis by direct measurement on the face and head of a subject, so as to eliminate the requirement of subjecting the patient to x-ray radiation.

BACKGROUND OF THE INVENTION

Lateral cephalograms (full-head x-rays, side view x-rays) are a well-known primary orthodontic analysis tool. Frontal view x-rays have been used to a lesser extent, in part because radiation dosage levels are several times higher and only twenty to thirty percent more information is obtained. Traditionally, a tracing is made of the lateral cephalogram (herein referred to as a "cephalometric tracing") and specific skeletal, dental and soft tissue measurements are then calculated from the tracing. The usual procedure is as follows:

First, a piece of standard tracing paper is fixed to the x-ray film. Next, outlines of key anatomical features are traced with a lead pencil. Then, various lines are drawn by connecting the anatomical landmarks with the aid of a straight edge. The particular lines depend upon the particular analysis or treatment of the patient which has been selected by the orthodontist. The distances between landmarks and angles between pairs of lines are calculated using a ruler and protractor. This information, called "cephalometrics", is used to described the patient's condition in an objective manner which can be communicated with others and used in research, education or diagnosis. If used for diagnosis, the values of these measurements can be the basis for determination of a specific treatment plan for a patient.

The location of certain "landmarks" within the facial complex is the primary information from which cephalometric analysis is made. The preparation of the tracing and identification of the precise location of the landmark teeth involve a certain amount of estimating and the process is far from being an exact science. A complete cephalometric analysis typically requires approximately one hour. Orthodontic schools have been teaching this general method of diagnosis and treatment for decades.

Although there are several variations of general cephalometric analysis, most rely on similar sets of measurements. For example, certain numerical values indicate whether or not to use head gear in treatment. Other measurements suggest a style of head gear to be used. Still others aid in elastic (rubber band) selection. Specific values indicate the magnitude and direction of incisor or molar movement required.

During orthodontic treatment of a patient, a number of cephalometric x-rays may be taken and tracings made in order to monitor the patient's progress toward the desired treatment goal. Additional cephalograms are taken at the end of treatment, and several years after completion of treatment, to determine the level of treatment success. In recent years, there has been reluctance to take such a number of x-rays as a result of concern over radiation exposure. Consequently, more recently orthodontists have not had access to valuable information which could facilitate and improve diagnosis and treatment.

There are a number of cephalometric analysis systems currently in use. The Downs Analysis is described in Downs, W. B., *Variation in facial relationships: Their Significance In Treatment and Prognosis*, 34 American Journal of Orthodontics, 812–840 (1948). The Steiner Analysis is described in Steiner, C. C., *Cephalometrics For Your And Me*, 39 American Journal of Orthodontics, 729–755 (1953). The Ricketts Analysis, both frontal and lateral, is described in Ricketts, et al., *Orthodontics Diagnosis And Planning*, published by Rocky Mountain Orthodontics of Denver, Co. in 1982. The McNamara Analysis is described in McNamara, J. A., *A Method of Cephalometric Evaluations*, 86 American Journal Of Orthodontics, 449–468 (1984). The Vari-Simplex Analysis is described in Alexander, R. G., The *Vari-Simplex Discipline*, published by Ormco Corporation of Glendora, Calif. in 1987.

There are certain main categories of data which are used in most cephalometric systems. The first is a patient classification by facial type. Patients with short, wide faces generally respond differently to specific types of treatments than patients with long, narrow faces. Positional data utilizing several external and accessible internal landmarks can be used to adequately categorize any patient by facial type. Relation of the upper jaw (maxilla) to lower jaw (mandible) is determined and is used by the orthodontist to determine if stimulation or inhibition of mandibular or maxillary growth is required to achieve a balanced profile The degree of incisor protrusion, angle of inclination, and the interrelations between upper and lower incisors can be found using a system which generates positional data. This information allows the orthodontist to reposition the teeth in harmony with both jaws, with each other, and with the soft tissue profile (nose, lips and chin).

The use of a computer to generate a cephalometric tracing is known in the art. For example the Ricketts et al. publication referred to above shows, in FIG. 165, a computer generated lateral cephalometric tracing. However, the tracing shown therein was derived from a secondary source of dimensional data, i.e., an x-ray. Consequently, the dimensional information is inaccurate for reasons inherent in the use of x-ray procedures as the source of dimensional data, such as non-linear distortion, as well as requiring that the patient be subjected to x-ray radiation in order to obtain the data.

SUMMARY OF THE INVENTION

The present invention provides a method for determining the location of a plurality of anatomical landmarks required for use in generating a cephalometric tracing of a head, including the steps of fixing the head with respect to a given reference, using a probe with a tip to identify directly the positions of pre-selected features on the head, generating digital data corresponding to the physical locations of such positions with respect to the reference, and calculating the locations of the required anatomical landmarks with respect to one another from such digitized data.

While the particular data points used vary from system to system, all systems are based upon the basic skull and tooth structure. Certain physical points, known as landmarks, which are used to generate the required data points for a particular system selected for use, cannot be measured directly by a non-invasive technique other than x-rays. However, since statistical studies are now available which correlate these "hidden" landmarks to directly measurable landmarks and directly measurable data points, algorithms can be generated by those ordinarily skilled in the art to be used in software programs to enable a computer to generate the cephalometric tracing, based upon the directly measured landmarks and data points. The landmarks particularly useful in this respect in the practice of the method of the present invention, which are generated by use of the algorithms from the directly measured data, are the roots of the teeth, the incisors in particular, and the skeletal landmarks such as the sella and the pogonion.

In practicing the invention, typically a patient's head is fixed with respect to a point of reference for the physical measurements to be taken directly from the patient by means of the probe tip. The head need not be fixed if a plane of reference for the head is established and digitized. Physical measurements of pre-selected landmarks on the patient's head are then generated in digitized form and utilized in a computer program to calculate diagnostic data points, as required for use in a cephalometric tracing. The computer program then generates the cephalometric tracing by connection the data points, and, if desired, adding straight lines and calculating angles and linear measurements as may be required for the particular orthodontic diagnosis system to be used. Additionally, at the time the digitized data is being generated, a video recording is made of the patient's head in the same planes in which the cephalometric tracings are to lie, and this recording is subsequently reproduced in visible form and combined with the cephalometric tracing as an overlay, one on the other.

While it is possible to generate digitized data in either three-dimensional form or two-dimensional form, in the preferred embodiment three-dimensional data is generated and is converted to two-dimensional data for presentation as a cephalometric tracing as, at present, three-dimensional cephalometric tracings are not normally used in practice.

The present invention provides apparatus for generating a cephalometric tracing of a head, having means for positioning the head with respect to a given reference and a probe having a tip, said probe having means for selectively transmitting position-indicating signals when the tip is at selected reference points. Means are provided for receiving the position-indicating signals transmitted by the probe and data processing means are provided to process the received signals so as to provide digital data corresponding to the locations of the probe tip with reference to the head corresponding to the selected reference points and to determine therefrom preselected anatomical landmarks. Means are provided with the preferred embodiment for displaying an image of at least part of the head from a chosen direction together with means for displaying on said image a cephalometric tracing from the same direction and to the same scale, formed by joining the appropriate anatomical landmarks generated by said data processing means.

BRIEF DESCRIPTION OF THE DRAWING

The invention may be more readily understood by reference to the accompanying drawings, in which.

DETAILED DESCRIPTION OF THE PREFERRED EMBODIMENT

Figure 1:
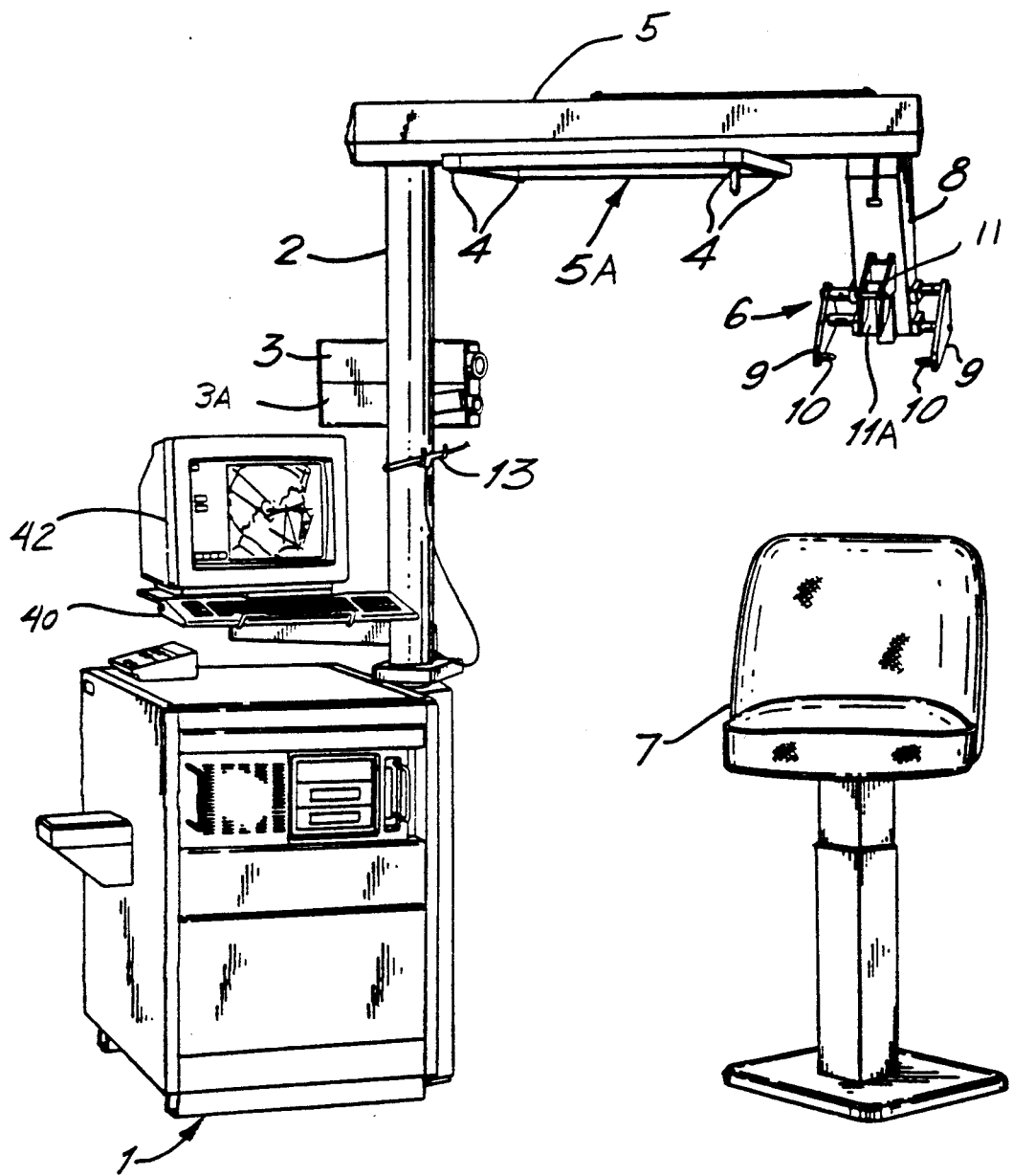
FIG. 1 is an isometric view of a complete system for use in accordance with the invention.

The method and apparatus of the present invention eliminate the prior art disadvantages referred to above by deriving dimensional information directly from the patient, rather than using a secondary source such as an x-ray negative.

In a presently preferred embodiment the initial step of the method comprises fixing the patient's head in space relative to a reference point to be used as the data base for the measurements. While for this purpose, conventional orthodontic head restraints may be used, in the preferred embodiment a novel restraint is provided. Alternatively, for example, a sensor could be fixed to the patient's head so as to provide a reference point for the measurements. The patient's head would not then be required to be immobilized. After a point or plane of reference is appropriately established with respect to the patient's head, digitized dimensional data is directly generated from the patient's head by suitable means. Various methods of generating such digitized information are presently known per se. Examples of three different methods are given in Rekow, D., *Computer-Aided Design And Manufacturing In Denistry; A Review Of The State Of The Art*, 58 The Journal Of Orthodontic Dentistry 512–516 (1987). A sonic ranging system may be utilized in U.S. Pat. No. 3,821,469 describes a three-dimensional sonic ranging system. Electromechanical and optical systems can be used to generate such digitized information directly. Other known methods are also applicable. Consequently, in its broadest aspect the method of the present invention is not limited to any particular system for generating the digitized dimensional data, so long as the data is generated directly from the subject, rather than from a secondary source.

In the presently preferred embodiment, a sonic ranging system with a hand-held probe is used to generate the data. The digitized dimensional information is generated by measurements of preselected landmarks on the patient's head. This dimensional data is utilized to calculate the required diagnostic data points for the particular analysis system being used. A computer program designed for the particular system of analysis is utilized to process the digitized data to calculate the diagnostic points for the cephalometric tracing. Once the data points are calculated, the cephalometric tracing is generated by use of a computer and a graphical plotter or other type of display to connect the data points so as to produce the tracing.

Obviously, it is within the capability of the computer program utilized to include the generation and superposition of straight lines required for the conventional pictorial presentation of the analysis, as well as measurements of the required angles for the conventional presentation of the completed tracing. In the preferred embodiment several different analysis systems can be selected. Each analysis system provides for different lines, angular measurements, and value print-outs. A master program which generates all required information for any number of systems, and selects therefrom the particular data required for the diagnostic system used, specified by the practitioner, is presently preferred. However, if desired, programs may be utilized which are limited to particular diagnostic systems. The computer program, irrespective of the system of diagnosis selected, generates dimensional data for the hidden landmarks by the use of algorithms based upon statistical data as to their location, in order to produce the cephalometric tracing in its currently conventional form.

In the presently preferred embodiment, three-dimensional digitized data is generated. Among the advantages of the method and apparatus is that a frontal cephalometric tracing can be generated as easily as a lateral tracing. Conventionally, frontal tracings have not been widely used, because of the greatly increased amount of radiation required for their generation as compared to the radiation required for the lateral x-ray. However, frontal tracings are extremely useful in practice of orthodontics or othognathic surgery in many instances, and their preparation is now practical by using the preferred embodiment, which generates the required three-dimensional data from which the computer program can derive the frontal tracing.

For orthodontic analysis, it is also useful to have a picture of the patient's head corresponding to the tracing, so that one may be overlaid on the other for comparison purposes. The preferred method and apparatus provides for the generation of such a picture by making a video recording of the subject at the time of the generation of the dimensional data. This video recording is then reproduced in conjunction with the presentation of the tracing, as either electronically overlaid or printed out and manually overlaid on the tracing.

While the preferred embodiment initially generates three-dimensional data, it is within the scope of the invention to generate two-dimensional data initially, rather than converting the three-dimensional data subsequently to two-dimensional data in the process of generating the tracing. By initially generating only two-dimensional data, the ability of the method and apparatus to produce both lateral and frontal tracings from the same set of digitized information is lost. However the complexity of the work station, including software programs and physical components, is greatly simplified if only two-dimensional data is to be acquired. Consequently, as frontal tracings are currently seldom used, for many applications of the present method, obtaining digitized two-dimensional data initially will suffice.

Because the method is non-invasive and does not involve irradiation of the subject's head, progress of orthodontic treatment can be readily monitored and recorded for archival purposes, as well as for facilitating the determination of the efficacy of the treatment being undertaken. The present method and apparatus permit a practitioner, if desired, to monitor the movement of even a single tooth during treatment, and to make any appropriate adjustments or modifications in the procedures as may be appropriate to ensure that the subject reaches an optimum result, without subjecting the subject to excessive radiation or invasive techniques.

Figure 2:
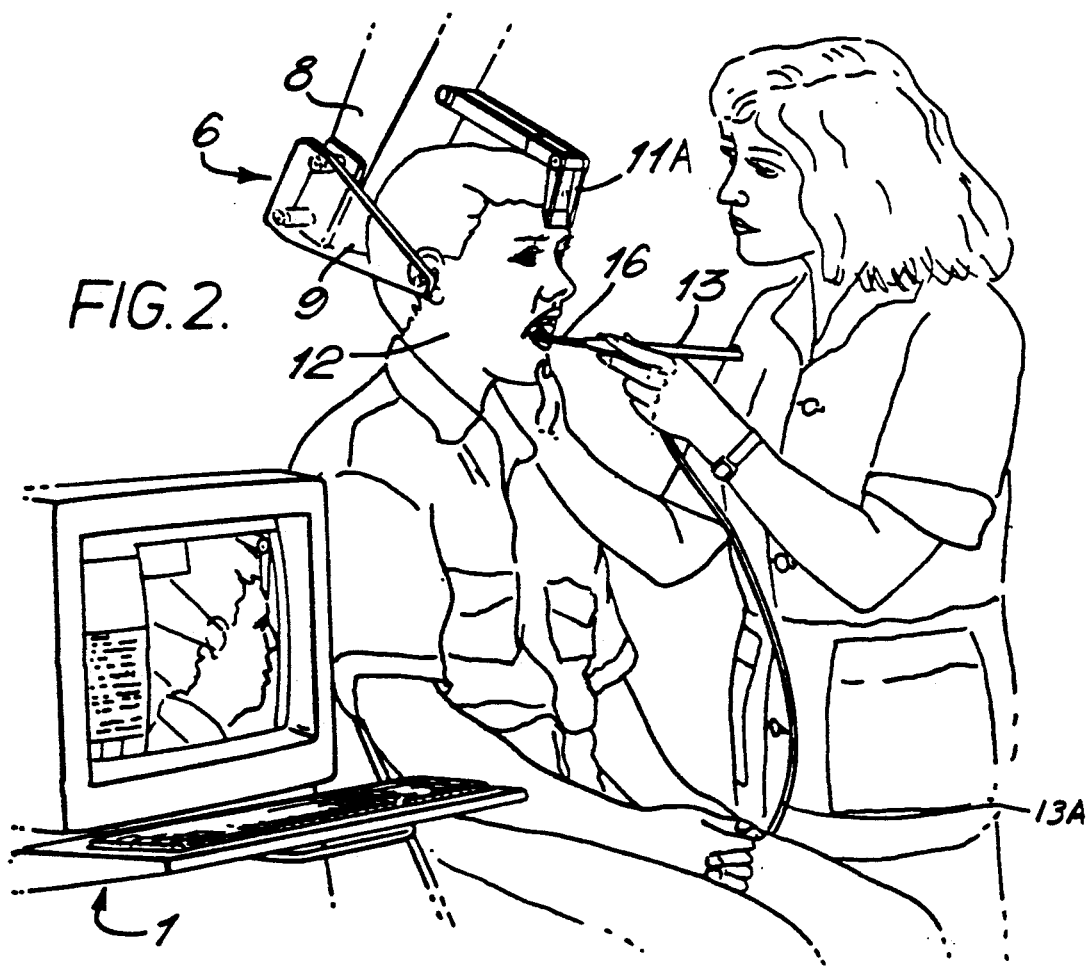
FIG. 2 is an enlarged view of part of the system of the present invention, showing it in use.

Referring now to FIGS. 1 to 4, a preferred embodiment of a cephalometric trace generating system according to the present invention includes data processing equipment 1 provided with a video display monitor 42, a support frame 2, a pair of vertically mounted video cameras 3, 3A with an intraoral telephoto lens mounted on the lower camera 3A, a planar array of four sonic receivers 4 mounted on a cross-bar 5 attached to the frame 2 by means of a rectangular sub-frame 5A, and a head restrainer 6 positioned over a seat 7 by being fixed to a rotatable downwardly projecting head restrainer arm 8 attached to the cross-bar 5. At the lower end of the arm 8 are two ear rod holder plates 9 with ear rods 10 attached for location in the ears of a patient, and a forehead arm 11 with an adjustable end holder 11A to engage the forehead of the patient. FIG. 2 shows a patient in place and having a head 12 held firmly but gently in place by the head restrainer 6.

The data processing equipment 1 typically includes a microcomputer which may, for example, have a 20 megabyte capacity, a 25 millisecond response time, and a 16 megahertz operating frequency with a computer graphics board for high speed image enhancement and manipulation such as a TARGA Model 16 distributed by True Vision, Inc. of Indianapolis, Ind.; a high resolution monitor with adequate pixel resolution for accurate landmark location on the display such as a Model 1312 Long Persistence Monitor distributed by Electrohome Electronics of Kitchener, Ontario, Canada; a conventional light pen not shown), the use of which is described hereinafter, which may be a Model 75 Light Pen, distributed by HEI, Inc. of Victoria, Me. with a Model Pixel Plus Light Pen Board distributed by Lite Pen Company of Los Angeles, Calif. for use in the interactive entry of data or commands; and an appropriate printer of conventional type used for hard copy output. The imaging system may use a 256 grey scale and may include two Model JE 3462 RGB video cameras distributed by Javelin Electronics of Torrance, Calif.

Figure 3:
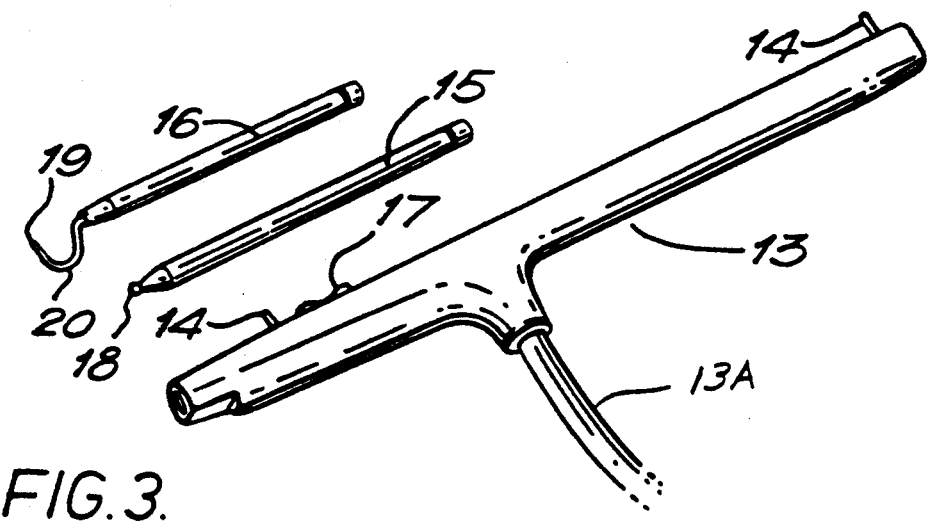
FIG. 3 is a view of a probe used on the present system, with two alternate tips.

As is shown in FIG. 3, the apparatus of the preferred embodiment also has a probe 13 which is linked to the data processing equipment 1 by a suitable cable 13A. The probe 13 has a pair of spaced sonic transmitters 14, a pair of interchangeable probe extensions 15, 16, and an actuator button 17. The probe extension 15 is adapted for use outside of the head and has a tip 18. The probe extension 16 is adapted for use inside the mouth and has a tip 19 at the end of a curve portion 20. The probe extensions 15, 16 are selectively fixed to the probe 13. Whichever of the probes 15, 16 is used, the probes are constructed so that each of the tips 18, 19 will be in an identical dimensional position relative to the remainder of the probe 13. Other probes can be provided for different purposes, such as data streaming the roof of the mouth or tracing the profile of the patient's head.

Probes and receivers of the general type shown are known, and are available, for example, as Model GP-8-3D Sonic Digitizer, manufactured by Science Accessories Corporation of Southport, Conn.

The four sonic receivers 4 are connected to the data processing equipment 1 and are positioned at the corners of the rectangular sub-frame 5A. The receivers 4 are adapted to receive sonic signals from the probe 13, which are produced by the two spaced transmitters 14 when the actuator button 17 is pressed. Since the position of the tip 18, 19 relative to the transmitters 14 is known, the data processing equipment 1 can process data from the receivers 4 to establish the position in space of the tip 18, 19 of the probe 13, using the time taken for each receiver 4 to detect the signal, and known triangulation techniques. Since in use the head 12 will be in a known fixed position, if the actuator button 17 is pressed while the tip of the probe is touching a selected position on the head 12, then the location of that position relative to the head can be calculated by the data processing equipment 1.

Figure 4:
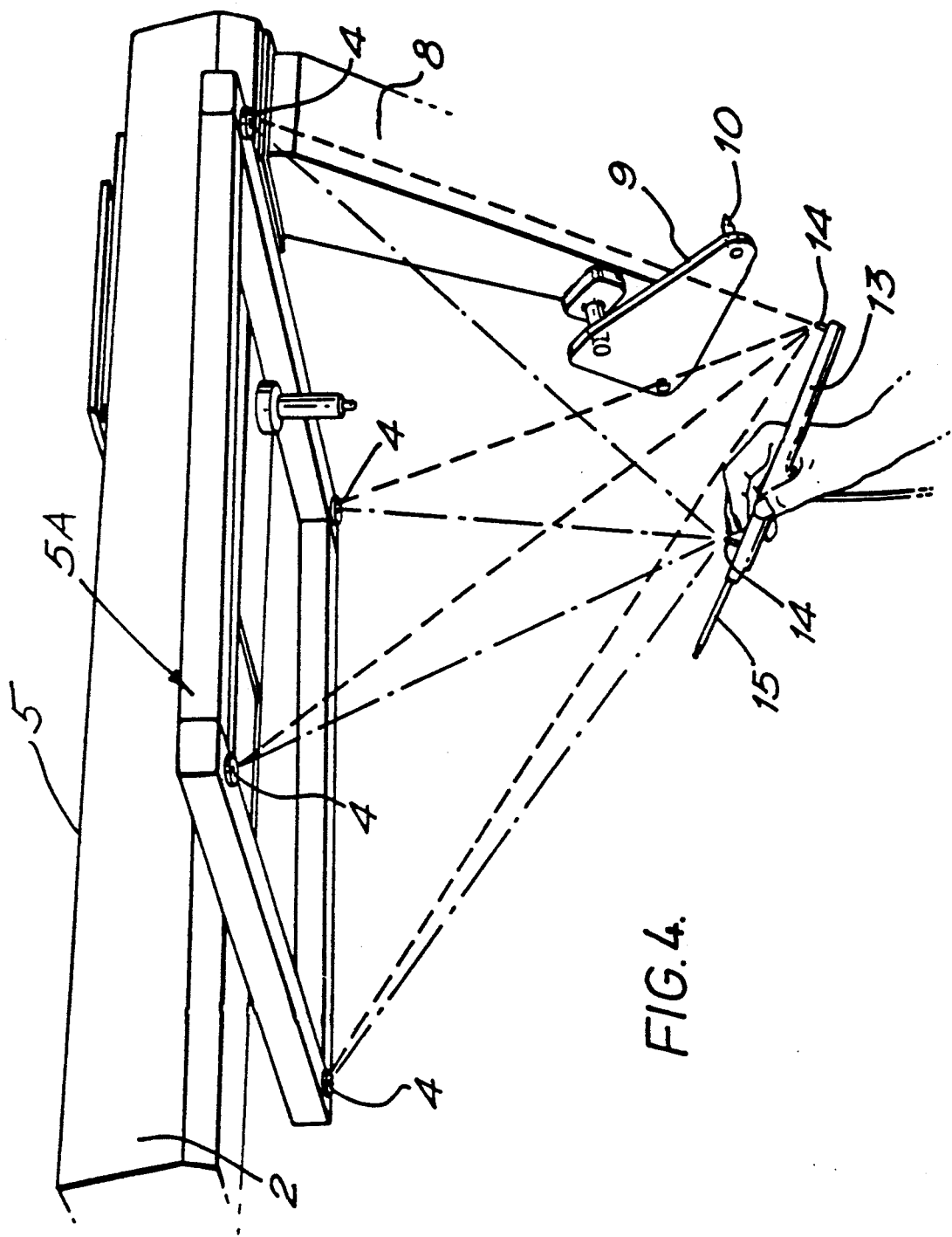
FIG. 4 is a diagrammatic view showing how the position of the probe tip is identified.

FIG. 2 shows the probe 13 with tip 19 (not shown) being used inside the mouth of a patient on a selected part of a selected tooth (not shown). When the actuator button 17 is pressed by the user, then the position of that part of the tooth will be calculated and recorded by the data processing equipment 1. FIG. 4 shows a diagrammatic view of a probe 13 with the actuator button pressed and transmitters 14 emitting sound waves that are received by the receivers 4. In certain embodiments, the transmitter 14 are actuated in multiple bursts with a single actuation of the button 17 and the resultant data statistically manipulated by the microprocessor to improve accuracy, if desired. Alternatively, transmitters similar to those shown on the probe 13 in FIG. 3 could be fixed to the patient's head 12 so as to provide a reference point or plane for the measurements, so as to obviate the necessity for immobilizing the head 12. Alternatively the probe can be a beam of light with the point of light (corresponding to the tip 18, 19 of the mechanical probe 13) on the landmark being viewed and triangulated by two fixed video cameras with their relationship in a known position relative to a given reference plane or, for three dimensional data generation, reference point.

In use, once the patient's head 12 is in position and the system correctly set up, the user can select the particular type of cephalometric analysis desired. In the presently preferred embodiment, there are fourteen analysis options, as follows:

Ricketts lateral
Ricketts frontal
Vari-Simplex
Holdaway
Alabama
Jarabak
Steiner
Downs
Burstone
McNamara
Tweed
Grummons frontal
Standard lateral
Standard frontal The various different analyses require different combinations of anatomical landmarks to be identified. Some of these landmarks are within the tissue of the head 12 and cannot be touched with the probe tip 18, 19. The system generates a list of selected anatomical points to be identified for the chosen analysis. The list is displayed in a logical order on a video monitor 42 to prompt the user to move about the face in a logical and convenient fashion, with the need to change the probe 13 extension only once if readings both inside and outside the mouth are required. In a typical exercise, the external points will be identified, then points within the mouth with the teeth in occlusion, and then a bite block is inserted and other points identified in the mouth. Usually about fifteen to thirty points have to be located. Some points will be readily observable and easy to locate; some may require palpation to be located; and some may require a little practice. However, all can be recognized eventually and located with the tip 18, 19 of the probe 13. The system display on the video monitor 42 highlights the next point to be located during a routine to locate points for the chosen analysis. Once the user has located the appropriate point, the actuator button 17 on the probe 13 is pressed and the position of the probe tip 18, 19, and thus the anatomical point, is recorded. The selected points can then be displayed on the video monitor 42 as superimposed on the video image of the patient obtained by the camera 3. Similarly, previous or future analyses can be superimposed imposed as the head 12 is held in the same position in each analyses.

Figure 5:
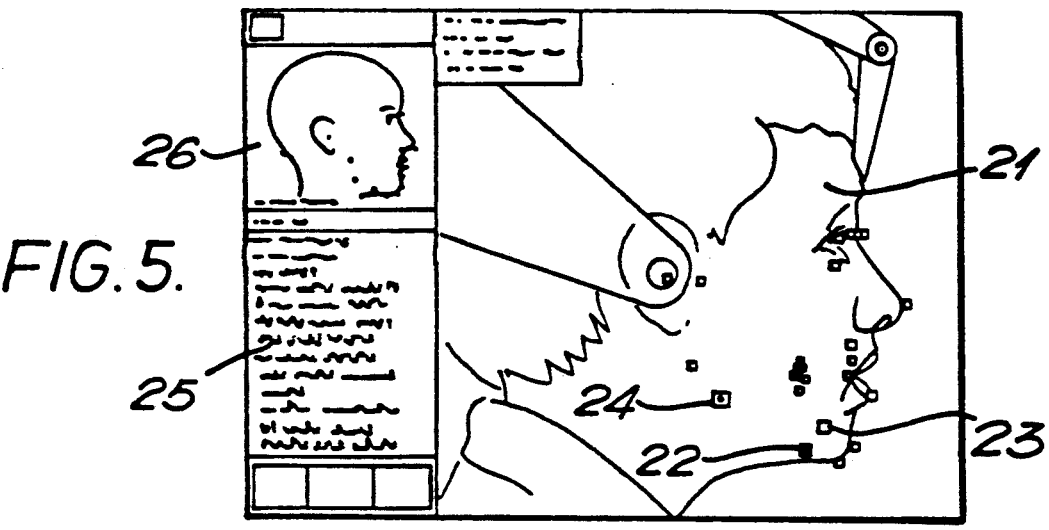
FIG. 5 is a view of a display according to the present invention showing the head of a patient on which anatomical landmarks have been superimposed.

In the presently preferred embodiment, as shown in FIG. 5, the video display includes the video image 21 of the head 12, on which are marked points already digitized such as 22, the point currently being digitized 23, and the next point to be digitized 24. Also displayed is a text box 25 containing instructions and a diagram 26 showing where the points are to be found. The box 25 and diagram 26 facilitate the detection of errors and their correction.

When a point has been located the landmark position related thereto may be known, or it may need to be calculated if it is not one that can be located directly. By way of example, the "hidden" landmark "sella" can be calculated based upon the locations of the following points:

1. A point on the cranium at a ninety-degree angle to Frankfort Horizontal through orbital.
2. A point at the back of the head which is the extension on the line through nasion and porion.
3. A point on the top of the head at a forty-five degree angle to Frankfort at porion.

Such a "hidden" landmark can be calculated from these points by the use of a suitable algorithm based upon available statistical data from studies which correlate the positions of hidden landmarks (which heretofore have been identified using x-ray techniques) to directly measurable points.

The data calculated initially by the system relates to the three-dimensional position information of the landmarks. The output to the display shows the landmarks projected in two dimensions, as is currently conventional. However, if an analysis requires, the display can be readily shown in three dimensions, as the data already exists to make this presentation. Once the landmark positions are known, the data processing equipment 1 produces the desired cephalometric tracing to be displayed on the monitor 42 by joining the various landmarks. If desired, two different types of tracing can be carried out and displayed superimposed along any desired axis.

Figure 6:
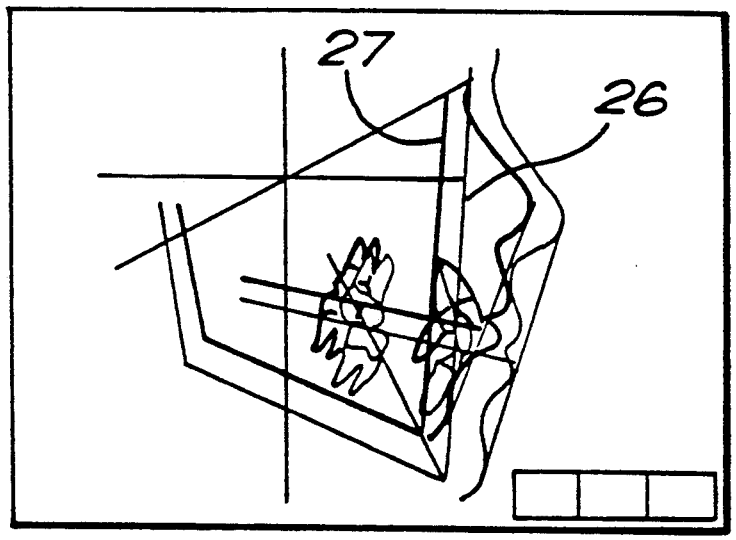
FIG. 6 is a view of a cephalometric tracing obtained using the present system.
Figure 7:
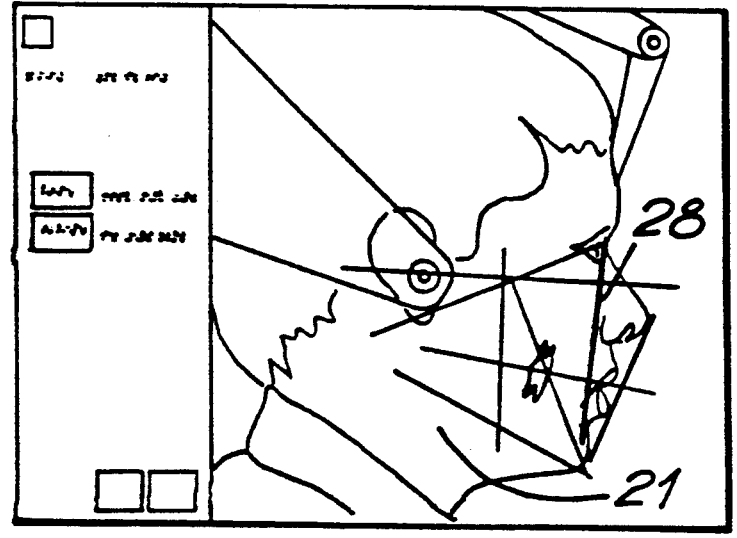
FIG. 7 is a view according to the present invention of the tracing superimposed on the head of the patient.

FIG. 6 shows two cephalometric tracings 26, 27 superimposed, each also including part of the profile of a patient's face. A cephalometric tracing, in the practice of the present invention, can be displayed over the video image of the patient, as shown in FIG. 7, where a tracing 28 is superimposed on the patient's head image 21. In this particular example, the profile obtained by the probe 13 can be used to check on alignment of the two images. The image displayed can be manipulated as desired, modified, have freehand drawings or text added, and so forth, using conventional software programs and hardware accessories.

A conventional light pen not shown) can be used to perform many functions in an interactive manner on the display, including moving and rotating the images. For example, a modified facial profile is generated and the cephalometric tracing modified accordingly. The reverse procedure can be followed. This process is utilizable to illustrate the results to be expected from different orthodontic procedures.

The data for a particular patient may be compared with norms obtained by statistical analysis, which may be adjusted for age, race, and sex. On the display significant deviations from the norm are highlighted, if desired. Comparative tabulated results are displayed, if desired. All data for a patient can be stored on suitable media such as magnetic or optical disks, and retrieved, updated or modified as desired. Information and images can be printed out using optional printers, when appropriate.

Figure 8:
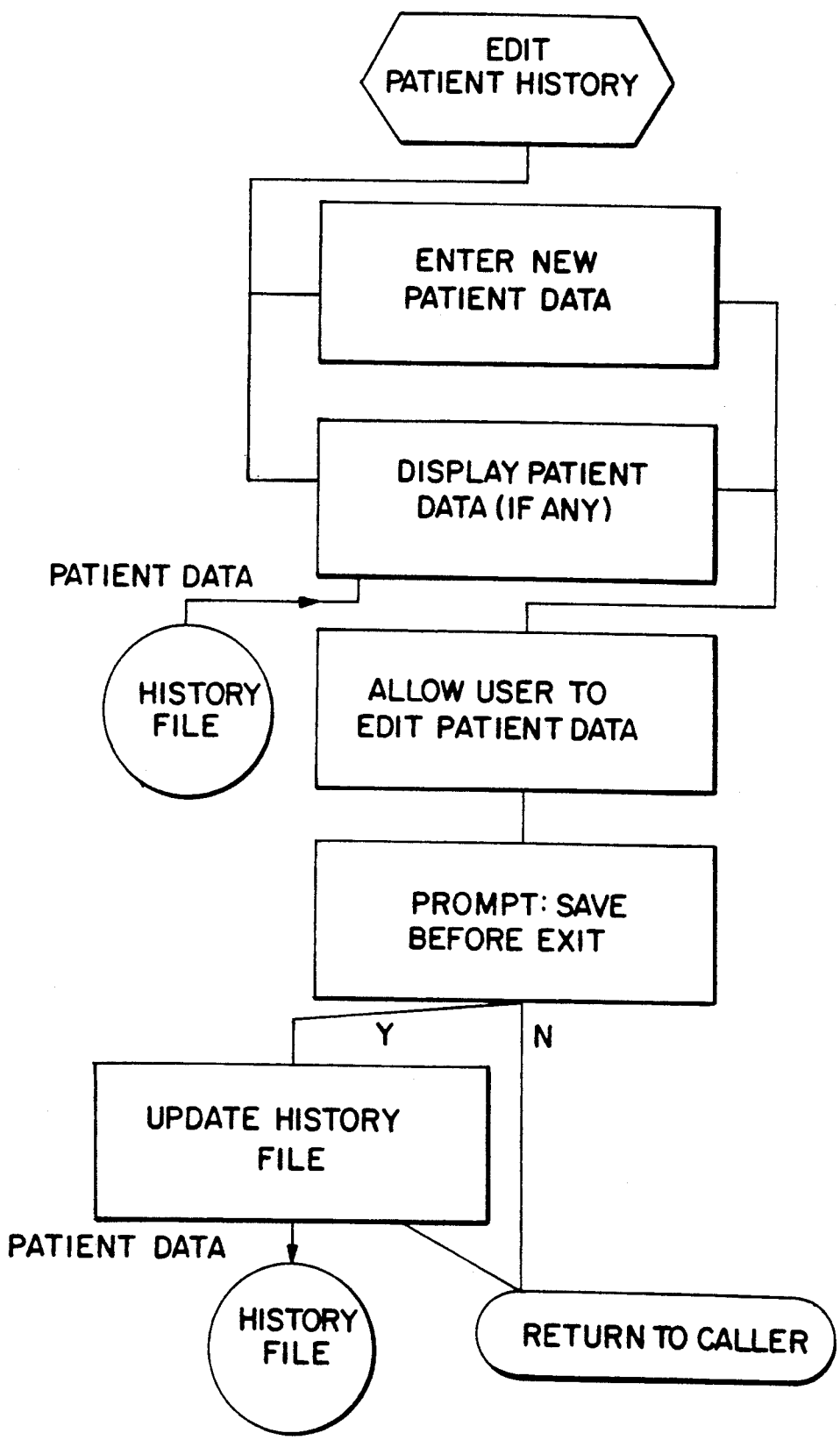
FIG. 8 is a computer program module data flow chart for use in the practice of the invention with a key board and a light pen to allow the user to enter patient information as is typical in current data base and office management systems.

Referring now to FIG. 8, a data flow chart is shown depicting the information flow for a software program whereby a patient history can be entered or modified by use of a light pen and/or a computer key board 40 (See FIG. 1) associated with a computer component of the data processing equipment 1. After the program is started, the first screen presented on the video monitor 42 prompts the user to enter new patient data or obtain patient data from a history file either on the computer hard disc or a floppy disc or other external digital storage. Included in this program is the ability to use time points for various records taken on a patient. The patient data is displayed on a patient records screen which shows data as the patient's name, ID number, birth date, race, dentition, age, race, sex, archival data plus any other desired information.

Figure 9:
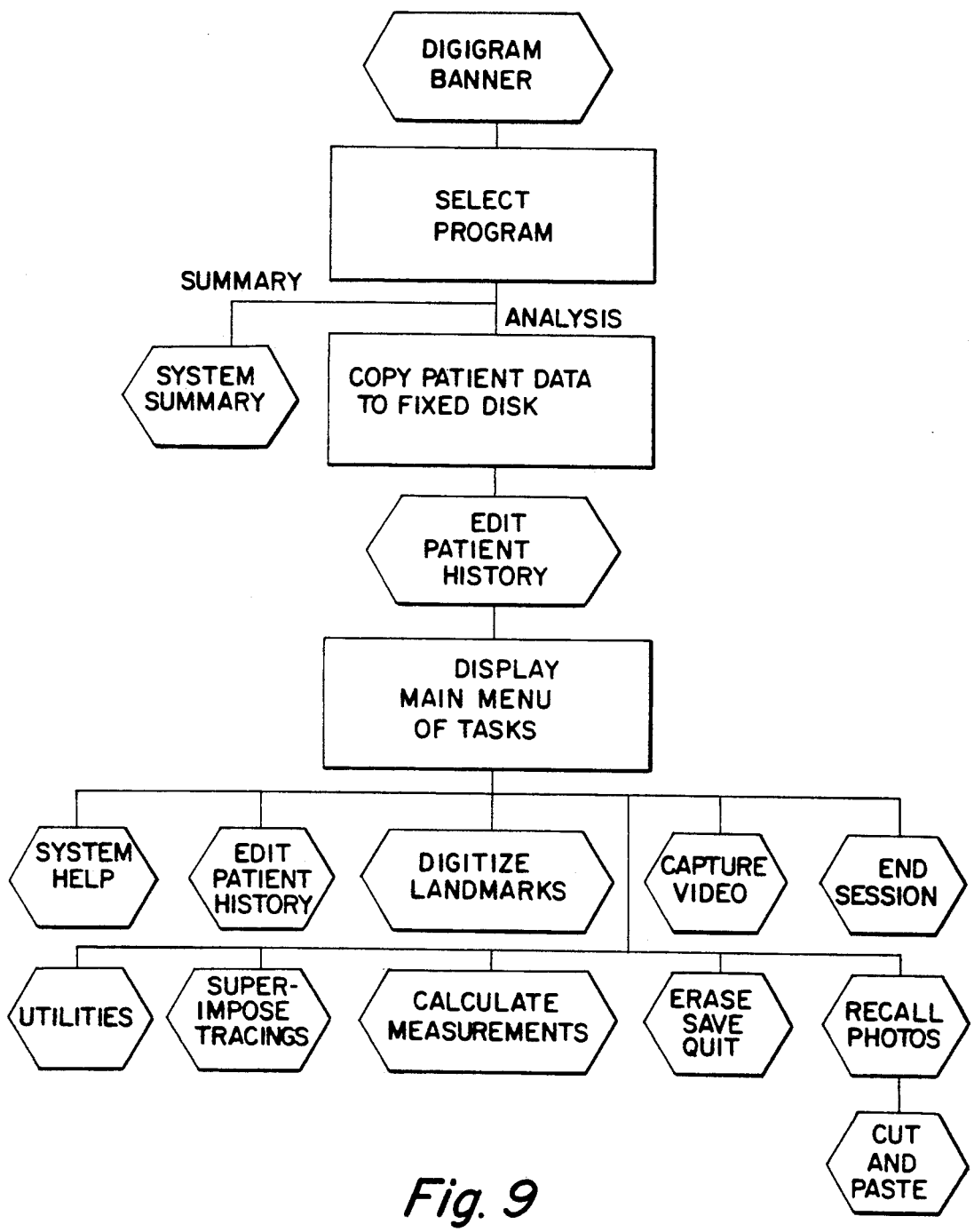
FIG. 9 is a data flow chart showing a computer program integrating all of the modules shown in FIGS. 8 to 18 and, in addition thereto, adding a visual treatment objective module.

After inputting the patient records, the main menu will appear on the monitor 40 (see FIG. 9). The selection options from this menu are "Edit Patient History," "Digitize Landmarks," "Capture Video," "Calculate Measurements," "Superimpose tracings," "Recall Photos," "Perform System Maintenance (Utilities)," "Help," "Quit," "Erase/Save," and "End the Session". Selecting "Help" produces an explanatory text as to when to make each selection. "Erase/Save" will begin the procedure to save the current patient's records to floppy disks (or other external storage) or will enable the user to remove a patient's information from the system hard disk. "Quit" will allow the user to exit the system.

Referring now to FIG. 9, a data flowchart is shown for the system summary portion of the software program. The "DigiGram Banner" program module is promotional and may also contain appropriate copyright information. The "Select Program" software module is a mechanical and computer screen switch to set up system functions such as calibration of the cameras, checking the squareness of the microphone array and the accuracy of the digitizer. Other software modules are shown in FIGS. 10-18, and will be discussed hereinafter. Additional modules can be added, such as Visual Treatment Objective, Links to Office Management Systems, Dental Cut and Paste Archives, or Surgical Modules, if desired.

Figure 10:
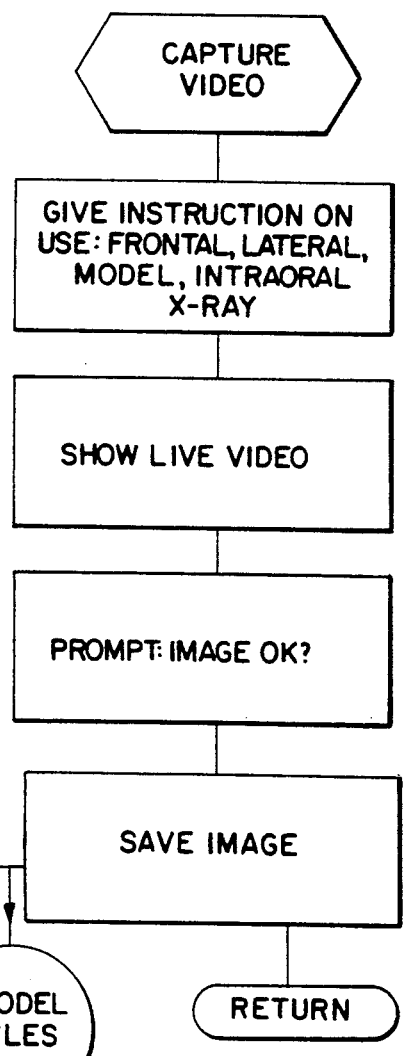
FIG. 10 is a flow chart showing a computer program module linking a color camera and a computer graphics system into the microprocessor according to the present invention.

FIG. 10 is a data flowchart for a software module showing the link between the computer targa graphics system and the video camera into the microprocessor. While in the capture video option of the main menu (see FIG. 9), the user may take five general categories of images with the video system through the Give Instructions On Use program module: Cephalometric, Facial, Intraoral, X-ray, and Model. Both lateral and frontal cephalometric images may be taken. All cephalometric images are taken with the patient positioned in the head restrainer 6 or, alternatively, a reference plane for measurements is established, as previously mentioned.

Also, the program allows facial photos of each patient to be taken, before, during and following treatment, without ear rods showing in the picture, by removal of the ear rod holders 9, and rotation of the head holder arm 8 so that the adjustable end portion 11 faces the camera 3. This procedure also permits intra-oral images to be taken using the lower camera with an appropriate telephoto lens with the light adjusted to the user's needs and room conditions. Intra-oral mirrors (not shown), as are used in existing systems, may be required to take certain of these images.

In the Give Instruction On Use "Model" section of the program module, to record a picture of an arch model, the user removes the ear rod holders 9 from the head holder arm 8, and fixes a model tray (not shown) to the head holder arm 8 in place thereof, places the model to be recorded on the tray, adjusts for height and then focuses utilizing the inter-oral arm of the video cameras 3.

For the "X-Ray" section of the Give Instructions On Use program module, the user removes the ear rod holders 9 from the head holder arm 8, fixes a light box (not shown) to the head holder arm 9, places the x-ray negative to be recorded on the light box and uses the facial camera.

In all of the above cases, the image is live and the user may make adjustments until it is frozen by utilizing the computer control, such as the key board, probe, or a foot switch.

An Red-Green-Blue ("RGB") camera system is shown in FIG. 10 as the preferred embodiment, where all lighting systems are external to the program. The TARGA graphics system includes a separate program module to adjust color, hue, and brightness of the screen image if a composite camera system is used. The user may also have external lights or reflectors to enhance the image. A separate program module may be added as a system enhancement; however, RGB systems are less sensitive to lighting conditions.

Figure 11:
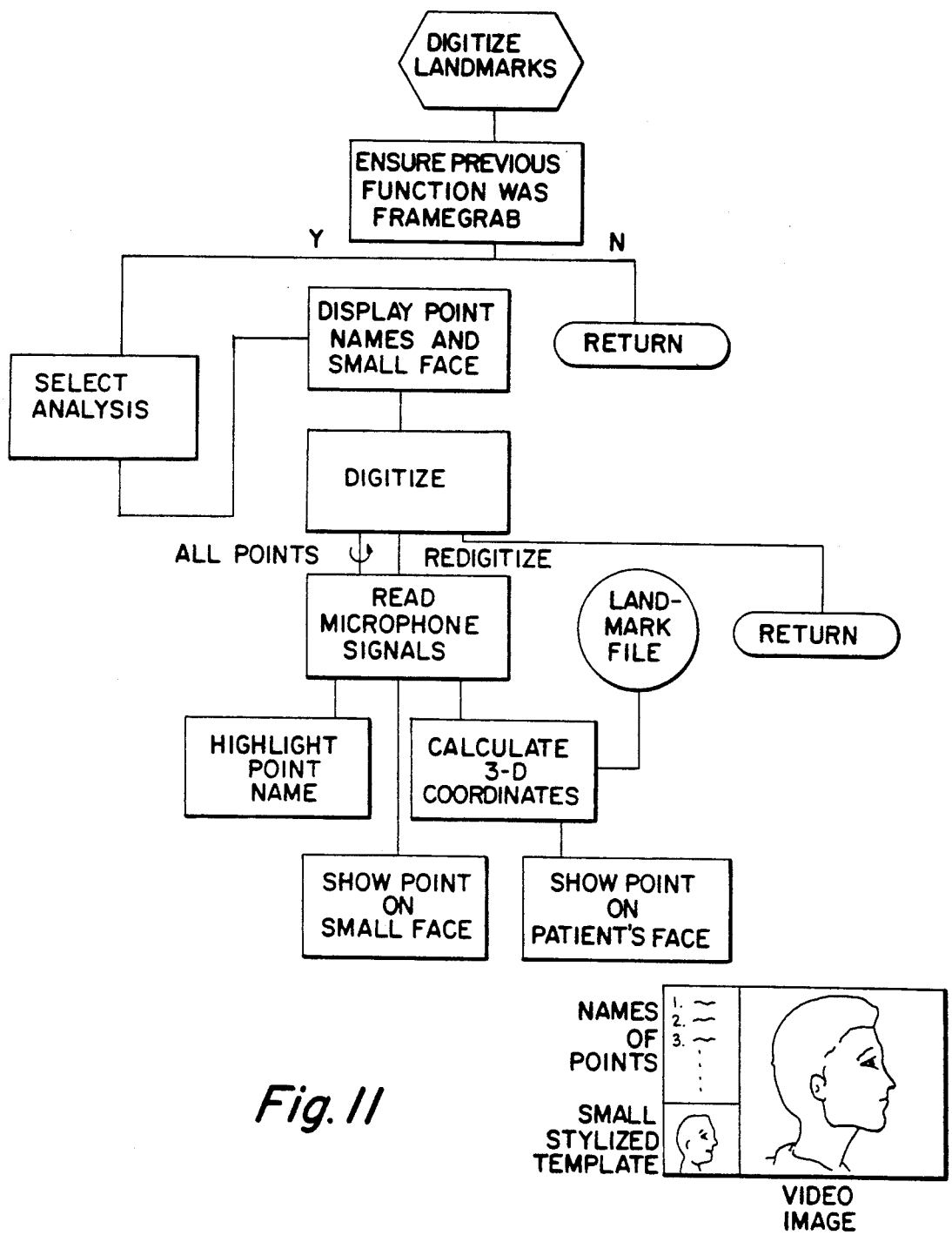
FIG. 11 a data flow chart for a computer program module utilizing slant algorithms to relate pre-selected facial location points identified by the doctor's choice of analysis when recognized by the microprocessor as the doctor touches the pre-selected point utilizing a probe and triggers sonic transmitters utilized to generate position signals.

FIG. 11 shows a data flowchart for use in determining the positions of landmarks, and includes a digitized landmarks module. Before the user digitizes lateral or frontal landmarks for a patient, the user should have already taken a video image of the patient for the corresponding view, i.e., lateral or frontal, at the current timepoint. Alternatively, the user may also digitize landmarks from a corresponding view of an x-ray negative by mounting the x-ray negative in the light box attachment, and digitizing landmarks using the probe 13.

After the requisite video has been taken, the user is transferred to the monitor screen to select the analysis to be utilized. As each analysis is selected it is highlighted. One or more analyses may be chosen or an analysis created. Once the analysis is fixed, the screen displays the point names and a small face to guide the user through the analysis.

The user now proceeds to digitize all points in the sequence prompted by the analysis selected. If any points appear suspect to the user or if the user makes a mistake in sequence, the user may scroll back or forward to that point and redigitize it. The computer reads the signals from the microphone and calculates, from the slant ranges as computed, for example, by a Science Accessories Corporation sonic digitizer comparable device, the resultant three dimensional coordinates for each point. At the same time, the program highlights the individual points on the video screen and shows the point digitized on the patient's face as previously described. This data is stored in a "Landmark File" for use in the "Calculate Measurements" module.

Figure 12:
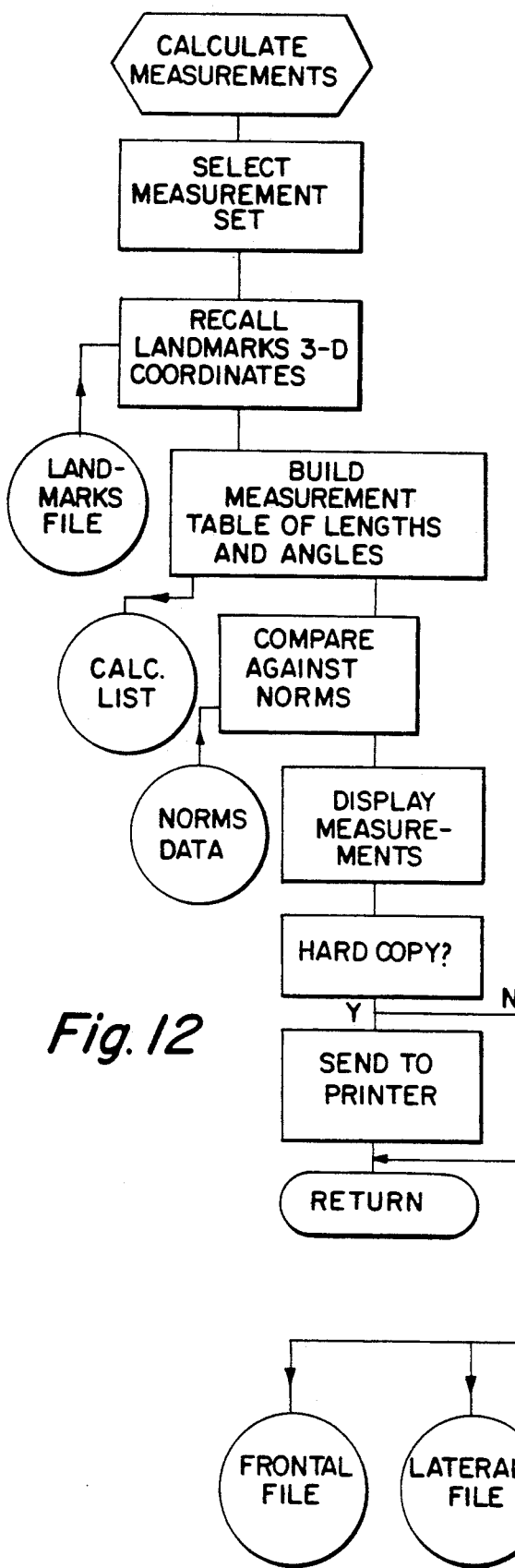
FIG. 12 is a data flow chart for a computer program module which is a compendium of normative cephalometric values for race, age, and sex constructed so that the user may compare the values determined in the digitized module to these normative values.

FIG. 12 shows a data flow chart for the "Calculate Measurements" module. In the "Select Measurement Set" module all digitized analyses for the patient are shown in a single name list. The light pen or keyboard may be used to select the analysis desired. The landmarks are then recalled and a measurement table of the lengths and angles is calculated and compared against normative values for race, age and sex. A hard copy is generated, if the user so directs.

Figures 13, 15:
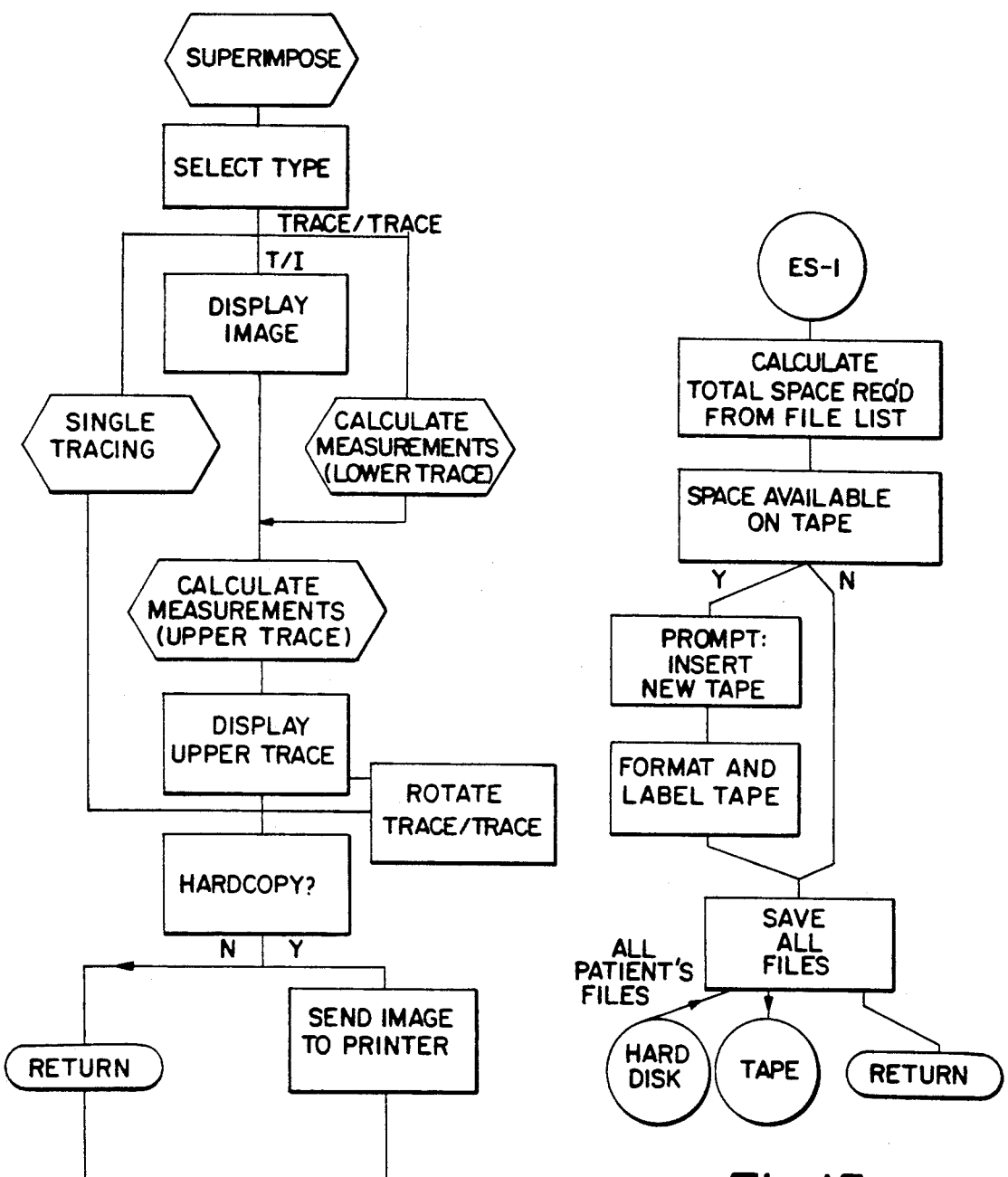
FIG. 13 is a data flow chart showing a computer program module which is a computerized representation of standard cephalometric tracings based on the digitized values with the capability of superimposing them on themselves and upon a fixed video image of the patient.
FIG. 15 is data flow chart showing a computer program module for checking file storage capacity in back up systems.

FIG. 13 shows a data flow chart for the "Superimpose" program module section. Any combination of three different activities may be performed when the user selects "Superimpose" at the "Main Menu." It is possible to superimpose tracings taken of the same patient at different timepoints. The user may superimpose a patient's tracing over a cephalometric video image. Additionally, the user may display the patient tracing at any timepoint on the monitor screen. In the tracing over tracing section the user also has the option of superimposing the tracing in several positions besides the relationship which initially appears on the screen. This resuperimposition is accomplished by using the light pen to drag one image into the desired relationship relative to the other. Alternatively, the program permits the keyboard arrow keys to be used to achieve the desired superimposition relationship.

The lower tracing, normally the current timepoint tracing, does not move. The upper tracing can be moved vertically, horizontally or rotated about any point until it is superimposed on the lower tracing at any point or line desired. Rotation about a point may be facilitated by use of a computer generated thumb tack actuated and moved by the light pen to define the point of rotation. A hard copy is generated upon command.

Figure 14:
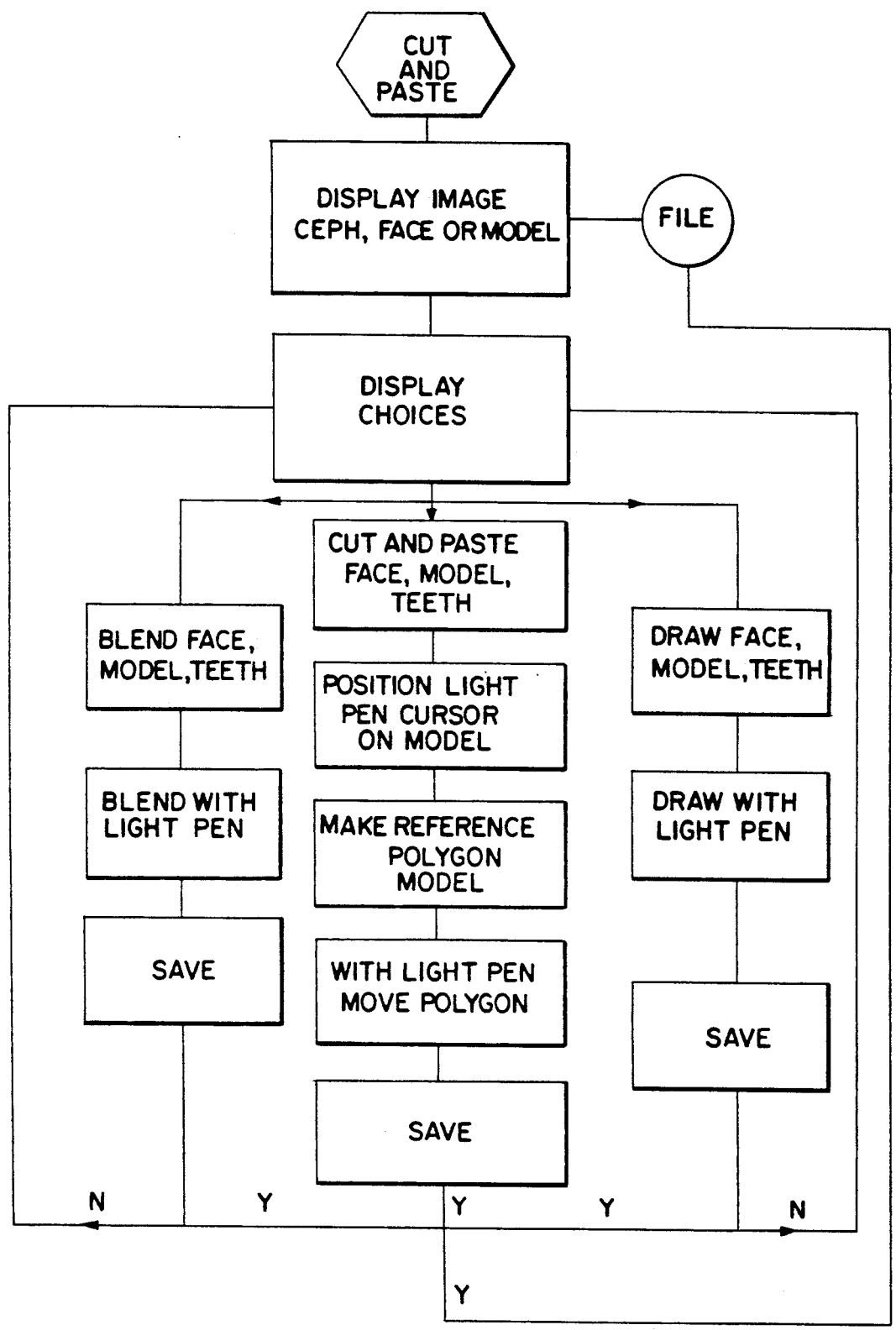
FIG. 14 us a data flow chart showing a computer program module which allows the doctor to generate representations of the patient's facial changes due to orthodontic treatment and/or surgical treatment, as appropriate, in which the doctor utilizes a light pen and a computer generated blending program.

FIG. 14 shows the "Cut and Paste" program module data flow chart. Any patient image (ceph, facial, intra-oral or model) can be modified using the cut and paste routines. The image to be modified is recalled from the file. The light pen is used to enlarge the image to be modified. The user then chooses between the "Blend," "Cut and Paste" and "Draw" options.

In the case of "Cut and Paste," the light pen cursor position is moved by touching the light pen to the video screen image to form the corners of a polygon, (the "cut") of as many sides as the user wishes to create. The light pen is then used to drag the polygon in any desired direction (the "paste") or the user can use the computer generated and light pen actuated thumb tack to rotate the polygon about any axis.

In modifying a cephalometric video image the landmarks associated with that image can also be modified. This modification ultimately changes the cephalometric tracing and measurements associated with the image. Thus, the user can create video visual treatment objectives and cephalometric visual treatment objectives simultaneously. The user can also see the modified cephalometric tracing superimposed on the modified video image.

The "Blend" function allows the user to take any color on the screen and blend it into an area with the light pen as a stylus. The "Draw" function allows the user to draw on the screen with the light pen The "Save" function allows the user to store the modified image for comparison to other images.

FIG. 15 shows a data flow chart for the program module for ending the session by first checking the space required for the data to be stored, then checking the chosen data archive system for space and, when required, prompting the user to insert a new data archive system and format and label the new system. When the process is completed, all files are saved to the system chosen.

Figures 16, 17:
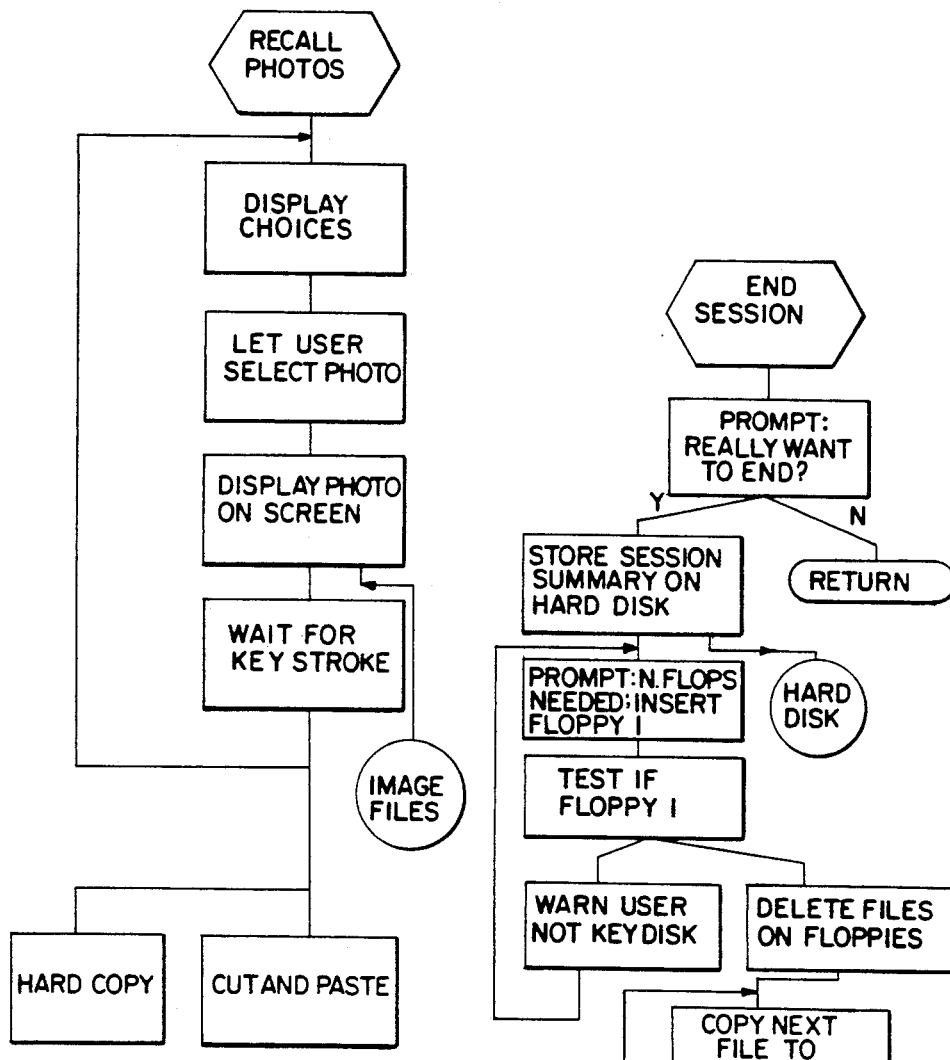
FIG. 16 is a data flow chart showing a computer program module for recalling fixed images taken with the video camera.
FIG. 17 is a data flow chart showing a computer program module for ending a digitizing session with a patient.

FIG. 16 shows a data flow chart for the program module for recalling photos or images already taken of a patient by showing those already taken on that patient, letting the user select the desired photo or image and displaying the photo or image on the screen from the image files. This module is used to show progressive or modified photos or images, generate hard copy and move into the Cut and Paste module.

FIG. 17 shows a data flow chart for the program module for "Ending the Session." The user is prompted as to whether to end the session. If so, the session summary is stored on hard disk and the user prompted to insert the "key disk" with the patient history. If the user has not inserted the "key disk," the program warns the user. This process is continued until all data is stored along with a back up data system, if desired.

Figure 18:
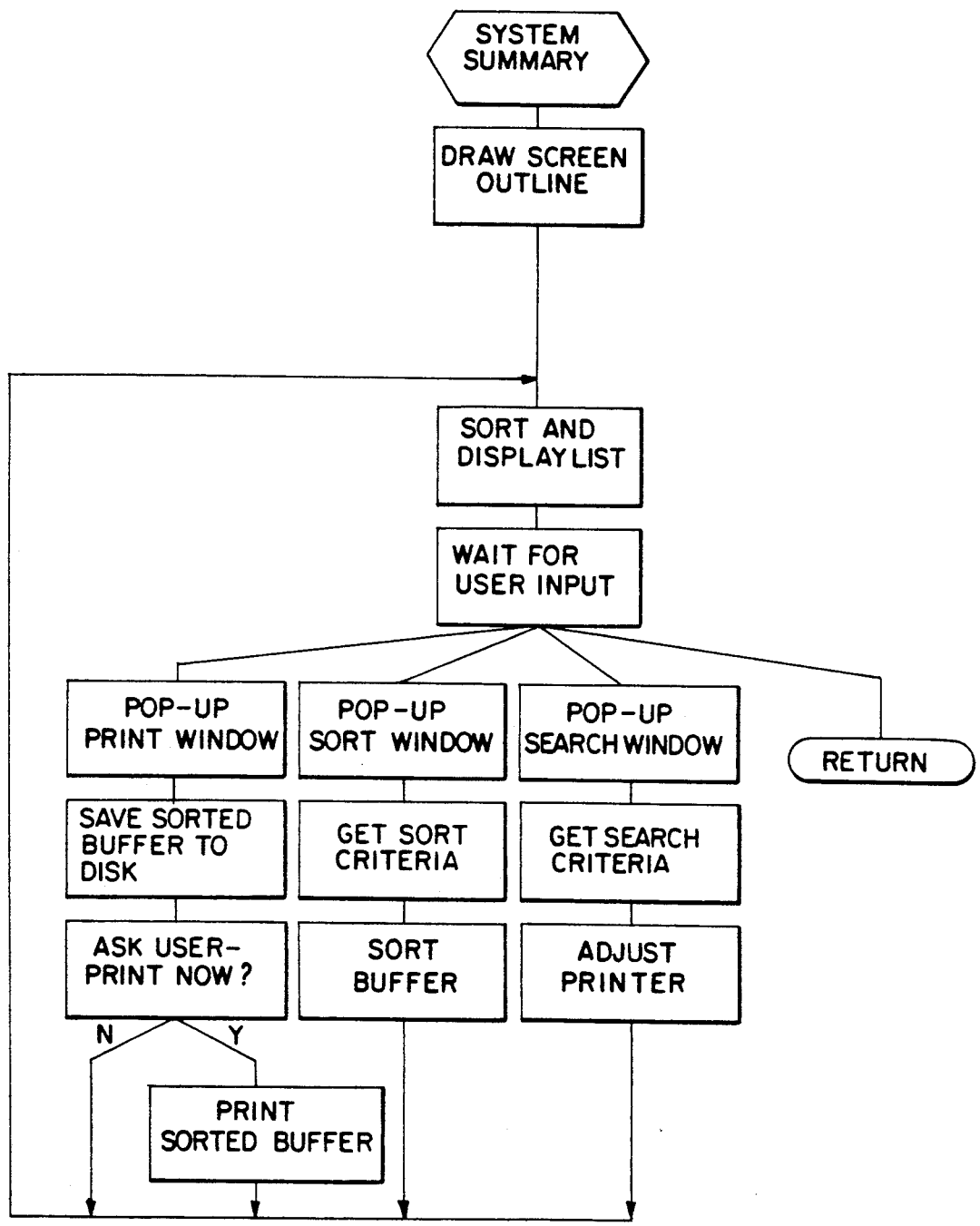
FIG. 18 is a flow chart showing a computer program module for the system summary portion of the program.

FIG. 18 shows a data flow chart for the program module for the "System Summary." This program first draws a screen outline and then sorts and displays lists of the data base. The user may elect to print the data in a pop-up window or sort the data and then print or search for specific data and then print. This function is used for manipulating the patient data as is currently done in most data base systems.

It will be understood by those familiar with the art that the flow charts described herein may be modified without departing from the present invention. The results obtained by the methods and flow charts are of use in orthodontic treatment and diagnosis but can also be used in research, education and so forth where a facial and dental profile and cephalometric analysis are desired.

It is apparent that the apparatus and method described herein may be modified without departing from the scope of the present invention. The results obtained by the method and apparatus are of use in orthodontic treatment and diagnosis but can also be used in research, education and so forth where a facial and dental profile are desired. Further, the apparatus and method can be used in place of x-ray techniques or subsequent to them in any analysis where the hard tissue is just under the soft tissue, readily accessible and identifiable through palpitation, and where pathology is not desired or appropriate, for whatever reason.

The invention claimed is:

1. A method for determining a location for each of a plurality of anatomical landmarks in a patient's head comprising the steps of:
   immobilizing said patient's head in a fixture;
   positioning a probe directly on positions of preselected visually observable physical features of said patient's head;
   establishing the physical positions of the preselected visually observable features with respect to the immobilized head in three dimensional space by detection of the position of said probe; and
   calculating the location of hidden anatomical landmarks which are not visually observable by a computer using statistical correlations of the hidden landmarks relative to the observable physical features.

2. A method as claimed in claim 1, including the step of connecting the anatomical landmarks to produce a cephalometric tracing.

3. A method for generating a cephalometric tracing directly from a patient for use in orthodontic diagnosis and treatment comprising the steps of:
   directly defining locations in three dimensional space of preselected visually observable landmarks by direct exterior measurement of the locations of the landmarks;
   establishing in a computer diagnostic points required for the cephalometric tracing from said directly defined locations of preselected visually observable landmarks including establishing visually nonobservable diagnostic points by use of statistical correlations between the visually nonobservable points and the preselected physically observable landmarks; and
   connecting the points so as to produce a cephalometric tracing.

4. The method of claim 3, and including the steps of:
   making a video recording of the patient's head corresponding to a spatial orientation of the cephalometric tracing simultaneously with said step of directly defining locations in three dimensional space of preselected visually observable landmarks by direct exterior measurement of the locations of the landmarks;
   producing a visible reproduction of said recording to the same scale as the cephalometric tracing; and
   superimposing one of the reproduction and the tracing on the other to provide an overlay of the tracing and the visible reproduction.

5. The method of claim 4 further comprising the step of converting said location in three dimensional space to a location in a selected plane to provide the points for the cephalometric tracing.

6. A method of determining a position of each of a plurality of anatomical landmarks of a patient, at least one of which landmarks is inaccessible exteriorly of the patent, comprising the steps of:
   establishing a fixed reference of measurement with respect to the patient by used of at least one position of a probe;
   sequentially positioning said probe on a plurality of preselected visible physical features of the patient;
   physically establishing a corresponding plurality of positions of the probe in three dimensional space relating to said visible features with respect to the fixed reference; and
   locating the position of at least one anatomical landmark exteriorly inaccessible to the patient by statistical extrapolation from the probe positions.

7. A method as claimed in claim 6 including the step of providing a visual display of the positions of the preselected features on a representation of at least part of the patient.

8. A method as claimed in claim 6 including the step of providing a visual display in the form of a cephalometric tracing in which the anatomical landmarks are joined by lines.

9. A method as claimed in claim 8 in which the visual display is reproduced o a representation of at least part of the patient's head.

10. A method as claimed in claim 9 in which the representation of the head is in the form of a camera image of the head obtained from the same direction as that of the visual display of the cephalometric tracing.

11. A method as claimed in claim 10 in which the cephalometric tracing includes a profile of part of the head obtained by moving the probe along the head.

12. A method as claimed in any of claims 6, 7, 8, 9 10 or 11, and in which the positions of the anatomical landmarks are determined in three dimensional form and converted for display in two dimensional form.

13. An apparatus for generating a cephalometric tracing of a patient's head comprising:

probe means including a tip to be placed at a plurality of preselected positions exterior to the patient's head, said probe means having means for selectively transmitting at least one signal when said probe means tip is placed on one of the preselected positions;

means for determining a fixed reference for measurements exterior to the patient's head from said probe means;

means for receiving signals transmitted by said probe means; and processing means for processing the received signals to establish the positions in three dimensional space of the probe means tip with respect to the fixed reference and for determining therefrom locations of anatomical landmarks which are interior to the patient's head based on statistical correlations stored within the processing means between the exterior measurements and interior anatomical landmarks.

14. Apparatus as claimed in claim 13 further comprising means connected to said processing means for displaying an image formed by joining appropriate anatomical landmarks.

15. Apparatus as claimed in claim 14, including a video camera to provide an image of the patient's head and means for digitally storing the image.

16. Apparatus as claimed in claim 13, wherein the means for determining the fixed reference for measurements includes means for producing an orientation reference signal, adapted to be accurately and repeatably positioned relative to the patient's head.

17. Apparatus as claimed in claim 16 wherein the probe means has interchangeable members carrying tips.

18. Apparatus as claimed in and of claims 13, 14, 15, 16 or 17, and in which the signals produced by the probe means are sonic.

19. Apparatus as claimed in claim 18 wherein said cephalometric tracing includes a tracing of tissue within a patient's head and, wherein the processing means is programmed to use at least one of the probe means tip positions in accordance with predetermined criteria in order to determine the positions of an anatomical landmark within the patient's head.

20. Apparatus as claimed in claim 19, including means for providing an output for advising a user of the apparatus as to the preselected positions at which the probe means tip is to be placed.

21. Apparatus as claimed in any of claims 13, 14, 15, 16 or 17, and in which the signals produced by the probe means are light.

22. Apparatus as claimed in claim 21, wherein the processing means is programmed to use at least one of the probe means tip positions in accordance with predetermined criteria in order to determine the position of an anatomical landmark within the head.

23. Apparatus as claimed in claim 22, including means for providing an output for advising a user of the apparatus as to the preselected positions at which the probe means tip is to be placed.

* * * * *